US008961822B2

(12) United States Patent
Abrams et al.

(10) Patent No.: US 8,961,822 B2

(45) Date of Patent: Feb. 24, 2015

(54) METALLOCARBENE COMPLEX PEROXIDE ACTIVATORS

(71) Applicant: Arkema Inc., King of Prussia, PA (US)

(72) Inventors: Michael B. Abrams, Bala Cynwyd, PA (US); Xiawei Zhang, West Chester, PA (US)

(73) Assignee: Arkema Inc., King of Prussia, PA (US)

( * ) Notice: Subject to any disclaimer, the term of this patent is extended or adjusted under 35 U.S.C. 154(b) by 134 days.

(21) Appl. No.: 13/792,749

(22) Filed: Mar. 11, 2013

(65) Prior Publication Data

US 2013/0190219 A1 Jul. 25, 2013

Related U.S. Application Data

(63) Continuation of application No. 12/990,317, filed as application No. PCT/US2009/043595 on May 12, 2009, now Pat. No. 8,414,793.

(60) Provisional application No. 61/052,718, filed on May 13, 2008.

(51) Int. Cl.

| | |
|---|---|
| ***C07D 295/15*** | (2006.01) |
| ***C11D 3/395*** | (2006.01) |
| ***C11D 3/16*** | (2006.01) |
| ***C11D 3/39*** | (2006.01) |

(52) U.S. Cl.

CPC .............. *C11D 3/3951* (2013.01); *C11D 3/168* (2013.01); *C11D 3/3932* (2013.01)

USPC ............ 252/186.39; 252/186.38; 252/186.41; 510/376

(58) Field of Classification Search

None

See application file for complete search history.

(56) References Cited

U.S. PATENT DOCUMENTS 6,241,779 B1 * 6/2001 Collins et al. .................... 8/111
6,462,007 B1 10/2002 Pieroni et al.
2005/0256017 A1 11/2005 Dvkstra
2006/0058514 A1 3/2006 Rottger et al.
2006/0173145 A1 8/2006 Pawlow et al.
2008/0033026 A1 2/2008 Zullo et al.

FOREIGN PATENT DOCUMENTS

WO WO 01/64825 A1 9/2001

OTHER PUBLICATIONS

Call et al. New generation of enzymatic delignification and bleaching. Pulp & Paper 106:1 (2005) 45-48.*

Sala et al. Synthesis of uracil derivatives by oxidation of Fischer tungsten-carbene uracil derivatives. Journal of Organometallic Chemistry 692 (2007) 1623-1627.*

Bourissou et al, "Stable Carbenes ", Chem. Rev. (2000), 100, pp. 39-91, American Chemical Society.

Voutchkova et al, "Disubstituted Imidazolium-2-Carboxylates as Efficient Precursors to N-Heterocyclic Carbene Complexes of Rh, Ru, Ir, and Pd", J. Am. Chem. Soc. (2005), pp. 17624-17625.

Weskamp et al, N-Heterocyclic carbenes: state of the art in transition-metal-complex synthesis, Journal of Organometallic Chemistry 600, (1999), pp. 12-22.

Blum et al, "Synthesis of N-Heteracylic Carbene-Containing Metal Complexes from 2-(Petafluoroplienyl)imidazolidines", Organometallics (2007), pp. 2122-2124.

* cited by examiner

*Primary Examiner* — Lorna M Douyon
*Assistant Examiner* — Tanisha Diggs
(74) *Attorney, Agent, or Firm* — Steven D. Boyd

(57) ABSTRACT

A bleaching composition comprising a peroxy compound and one or more activator present in an effective amount to activate the peroxy compound, present in an amount effective to accomplish bleaching or cleaning or oxidation. The activator is a metallocarbene of the general structure $(XX'C)_yML_n'$ where M represents a metal center, C represents the carbene carbon bound to the metal center, X and X' may be the same or different and may furthermore be part of a cyclic structure, $L_n'$ represents one or more other ligands which may or may not include one or more metal centers, and where y≥1.

10 Claims, No Drawings

METALLOCARBENE COMPLEX PEROXIDE ACTIVATORS

This application is a continuation of and claim priority benefit of U.S. application Ser. No. 12/990,317 filed Oct. 29, 2010 now U.S. Pat. No. 8,414,793, which claims priority benefit of international application serial number PCT/US09/43595 filed May 12, 2009 which application designated the United States which claims priority benefit of U.S. provisional application Ser. No. 61/052,718 filed May 13, 2008.

FIELD OF THE INVENTION

This present invention relates to the use of metallocarbene complexes in the activation of bleaches employing peroxy compounds, including hydrogen peroxide or a hydrogen peroxide adduct. The present invention also relates to bleach compositions, including detergent bleach compositions, which contain metallocarbene activators for peroxy compounds; and to processes for bleaching, washing, and/or oxidation of substrates employing the aforementioned types of compositions.

BACKGROUND OF THE INVENTION

Materials that react beneficially with hydrogen peroxide are needed for a wide variety of applications. For laundry detergents, for example, substances that reacts with hydrogen peroxide to provide improved stain bleaching (versus peroxide alone or versus alternatives) are highly desirable. Hydrogen peroxide alone does not provide sufficient bleaching on all stains of interest, often does not provide sufficient stain bleaching at low temperatures, or does not bleach quickly enough at elevated temperatures to match the performance of existing alternatives. Current organic activators for hydrogen peroxide, such as peracid generators currently used for solid laundry detergents, typically operate stoichiometrically, providing economic challenges to practical implementation. It is known that many transition metal ions catalyze the decomposition of $H_2O_2$ and $H_2O_2$-liberating per-compounds, such as sodium perborate. It has also been suggested that transition metal salts together with a coordinating or chelating agent can be used to activate peroxide compounds so as to make them usable for satisfactory bleaching at lower temperatures or to provide enhanced bleaching performance at a given temperature. Current commercial metal-based activators suffer from deficiencies in one or more of the following areas: poor bleaching (oxidative) activity, fabric safety, poor solubility, prohibitively expensive economics, poor environmental fate profiles. The ability to more effectively use hydrogen peroxide (whose sole degradation products are water and oxygen) could reduce the use of potentially harmful chlorine-based bleaches e.g. sodium hypochlorite for cleaning, or chlorine dioxide for pulp and paper. Iron (Fe), manganese (Mn), cobalt (Co), and copper (Cu) are relatively inexpensive metals. A hydrogen peroxide activation catalyst employing any of these metals can provide significant economic and health/environment/safety advantages compared to current existing alternatives. Peroxide activators based on other metals are also of interest.

SUMMARY OF THE INVENTION

The present invention is directed towards the use of metallocarbene complexes in the activation of bleaches employing peroxy compounds. As used herein, activation refers to catalytic and/or non-catalytic actions. The metallocarbene complexes of the present invention are of the general structure:

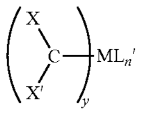

where M represents a metal center, C represents the carbene carbon bound to the metal center, X and X' may be the same or different (and may furthermore be part of a cyclic structure), and are preferably selected from the group C, N, O, Si, P, or S, each of which may be substituted with hydrogen and or C1-C20 linear or branched hydrocarbons which may furthermore contain heteroatom substituents and which may form or be part of a cyclic structure. $L_n'$ represents one or more species (which independently represent a coordinating or bridging ligand or non-coordinating species, and may or may not include one or more metal centers), preferably selected from the group $H_2O$, ROH, ROR, $NR_3$, $PR_3$, RCN, $HO^-$, $HS^-$, $HOO^-$, $RO^-$, $RCOO^-$, $F_3CSO_3^-$, $BF_4^-$, $BPh_4^-$, $PF_6^-$, $ClO_4^-$, $OCN^-$, $SCN^-$, $NR_2^-$, $N_3^-$, $CN^-$, $F^-$, $Cl^-$, $Br^-$, $I^-$, $H^-$, $R^-$, $O_2^-$, $O^{2-}$, $NO_3^-$, $NO_2^-$, $SO_4^{2-}$, $RSO_3^-$, $SO_3^{2-}$, $RBO_2^{2-}$, $PO_4^{3-}$, organic phosphates, organic phosphonates, organic sulfates, organic sulfonates, and aromatic N donors such as pyridines, bipyridines, terpyridines, pyrazines, pyrazoles, imidazoles, benzimidazoles, pyrimidines, triazoles, and thiazoles, and can include one or more additional carbene ligands, and where y≥1 and preferably from 1 to 4. R can be the same or different and be hydrogen, alkyl, aryl, substituted alkyl, substituted aryl, and mixtures thereof. The use of Fe, Mn, and Cu as the metal (M) are preferred however, metallocarbene catalysts based on Co, Mo, W, V, and Ti, and other suitable metals are within the scope of the present invention.

There are many potential structural variations on the above carbene ligand framework, including, but not limited to:

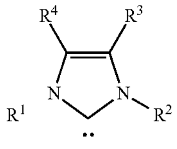
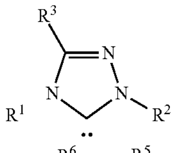
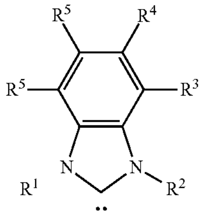
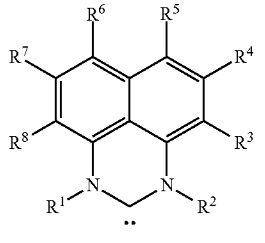
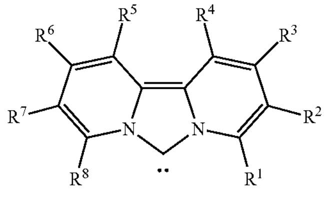
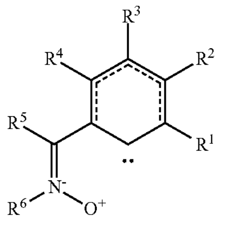

-continued

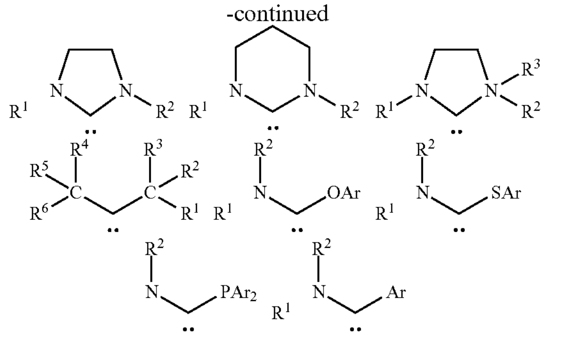

The carbene ligand substituents $R^1$-$R^{11}$ may be the same or different. They may be hydrogen or C1-C20 linear or branched hydrocarbons, including but not limited to methyl, chloromethyl, ethyl, propyl, isopropyl, tert-butyl, sec-butyl, n-butyl, pentyl, n-hexyl, cyclohexyl, heptyl, octyl, nonyl, lauryl, adamantyl, benzyl, phenyl, substituted phenyls such as chlorophenyl, dichlorophenyl, methylphenyl, nitrophenyl, aminophenyl, dimethylphenyl, pentafluorophenyl, methoxyphenyl, trifluoromethylphenyl, bis(trifluoromethyl)phenyl, 2,4,6-trimethylphenyl, 2,6-diisopropylphenyl groups and may furthermore have one or more heteroatom containing group including but not limited to halides, amines, amides, pryidyls, ethers, aldehydes, ketones, phosphines, and sulfonates. Ar denotes an aryl group, which may be substituted with one or more hydrogen or C1-C20 linear or branched hydrocarbons which may contain hetroatom substituents, including but not limited to methyl, ethyl, propyl, isopropyl, tert-butyl, sec-butyl, n-butyl, pentyl, n-hexyl, cyclohexyl, heptyl, octyl, nonyl, lauryl, adamantyl, benzyl, phenyl, substituted phenyls such as chlorophenyl, dichlorophenyl, methylphenyl, dimethylphenyl, pentafluorophenyl, methoxyphenyl, nitrophenyl, aminophenyl, trifluoromethylphenyl, bis(trifluoromethyl)phenyl, 2,4,6-trimethylphenyl, 2,6-diisopropylphenyl groups, and may furthermore have one or more heteroatom containing groups including but not limited to halides, amines, amides, pryidyls, ethers, aldehydes, ketones, phosphines, and sulfonates. The carbenes can incorporate zwitterions such as the nitrons shown. The metallocarbenes may be chiral, either by incorporation of one or more chiral substituents on the carbene ligand, by the arrangement of various substituents on the carbene ligand, and/or by arrangement of the various groups around the metal center.

The present invention encompasses activators with one or more carbene groups. In activators with more than one carbene groups, the individual carbene groups may either be the same or different. Exemplary substitutions of the carbene ligand or ancillary ligand arrays are provided herein below.

Examples of polydentate carbene ligands include not only bis(carbene) ligands, tris(carbene) ligands, and higher poly (carbene) ligands, but also carbene ligands with one or more non-carbene groups capable of coordinating to a metal center, including but not limited to, the structures shown and described below.

Procedures for generating N-heterocyclic carbene ligands are known, including but not limited to deprotonation of azolium salts, oxidative addition of azolium salts, $CO_2$ elimination, and $C_6F_5$ elimination; see, for example, *Chem. Rev.,* 2000, 100, 39, *J. Organomet. Chem.,* 2000, 600, 12, *J. Am. Chem. Soc.,* 2005, 127, 17624, *Organometallics,* 2007, 26, 2122, and references therein.

Metallocarbene complexes may be made by several methods, including the addition of metal precursors to preformed carbene ligands, the use of silver transmetalating agents, or by in situ generation and complexation of the carbene ligand with a suitable metal precursor. One alternate potential method for generating activators for use in cleaning in accordance with the present invention (e.g. laundry) is to add carbene ligand or a suitable precursor to the wash liquor, and to generate the activator in situ through complexation of the ligand(s) with metal ions occurring naturally in the water used to make up the wash liquor.

Although hydrogen peroxide is a preferred oxidant, the activators of the present invention could alternately, or in addition, provide activation in conjunction with other peroxides, for example alkylhydroperoxides, dialkylperoxides, peracids, inorganic perhydrate salts, including alkali metal salts such as sodium salts of perborate (usually mono- or tetrahydrate), percarbonate, persulfate, perphosphate, persilicate salts, and/or dioxygen. Also within the scope of this invention are bleaching processes with and compositions of the activators described and sodium percarbonate, sodium perborate, or other materials that generate peroxides or peracids.

The activators of the present invention can be used in applications, including, but not limited to:

Cleaning: general fabric cleaners including but not limited to liquid or solid laundry detergents, auxiliary bleaches, prespot treating agents, and general household cleaners including but not limited to automatic dishwashing detergents, hard surface cleaners, toilet bowl cleaners, carpet cleaners, heavy duty cleaners, fence/deck/siding cleaners, drain cleaners, and specialty cleaners.

Pulp and paper: bleaching, brightening, and delignification in mechanical and chemical pulping, and deinking during paper recycling.

Personal care: antiseptic applications, hair bleaching and coloring, tooth whitening and oral care.

Chemical processes: general oxidation reactions including but not limited to epoxidation, hydroxylation, bromine reactivation, organic peroxide production, amine oxidation, processes for chemical or pharmaceutical synthesis or manufacture, as well as decolorization.

Textile or Fiber Bleaching

Environmental: water treatment, wastewater or storm water treatment, including but not limited to pollutant degradation and decolorization, and wastewater or storm water odor reduction or elimination.

General broad-spectrum disinfection and sanitization, mold/mildew, spore, virus, fungus removers.

Defense: chemical or biological warfare agent degradation

Bioethanol: improved delignification for increased cellulosic ethanol production Desulfurization of diesel fuel, gasoline, kerosene, biodiesel, or coal

DETAILED DESCRIPTION OF THE INVENTION

The present invention relates preferably to the use of metallocarbene complexes as hydrogen peroxide activators; that is to say that the metal-containing complex reacts with hydrogen peroxide to form a species that provides superior oxidation performance (e.g. stain bleaching or pulp bleaching).

The metallocarbene complexes of the present invention are of the general structure 1:

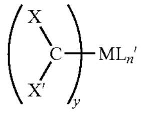

(1)

where M represents a metal center preferably selected from Fe, Mn, Cu, Co, Mo, W, V, and Ti, or other suitable metals, C represents the carbene carbon bound to the metal center, X and X' may be the same or different (and may furthermore be part of a cyclic structure), and are preferably selected from the group C, N, O, Si, P, or S, each of which may be substituted with hydrogen and or C1-C20 linear or branched hydrocarbons which may furthermore contain heteroatom substituents and which may form or be part of a cyclic structure. The use of Fe, Mn, and Cu as the metal (M) are preferred however, metallocarbene catalysts based on Co, Mo, W, V, and Ti, and other suitable metals are within the scope of the present invention. $L_n'$ represents one or more ligand species (which independently represent a coordinating or bridging ligand or non-coordinating species, and may or may not include one or more metal centers), preferably selected from the group $H_2O$, ROH, ROR, $NR_3$, $PR_3$, RCN, $HO^-$, $HS^-$, $HOO^-$, $RO^-$, $RCOO^-$, $F_3CSO_3^-$, $BF_4^-$, $BPh_4^-$, $PF_6^-$, $ClO_4^-$, $OCN^-$, $SCN^-$, $NR_2^-$, $N_3^-$, $CN^-$, $F^-$, $Cl^-$, $Br^-$, $I^-$, $H^-$, $R^-$, $O_2^-$, $O^{2-}$, $NO_3^-$, $NO_2^-$, $SO_4^{2-}$, $RSO_3^-$, $SO_3^{2-}$, $RBO_2^{2-}$, $PO_4^{3-}$, organic phosphates, organic phosphonates, organic sulfates, organic sulfonates, and aromatic N donors such as pyridines, bipyridines, terpyridines, pyrazines, pyrazoles, imidazoles, benzimidazoles, pyrimidines, triazoles, and thiazoles, and can include one or more additional carbene ligands, and where $y \geq 1$, preferably from 1 to 4. R can be the same or different and be hydrogen, alkyl, aryl, substituted alkyl, substituted aryl, and mixtures thereof.

There are many potential variations on the above carbene ligand framework; the following description will focus on the framework of structure 1, although any of the metallocarbenes or variations thereof described herein are envisioned by the present invention.

Preferred structures include

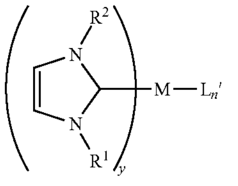

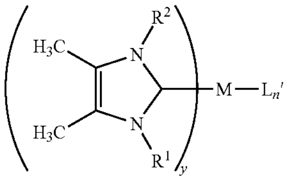

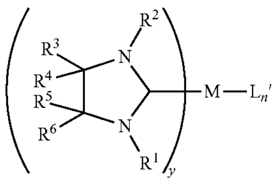

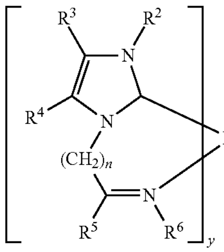

-continued

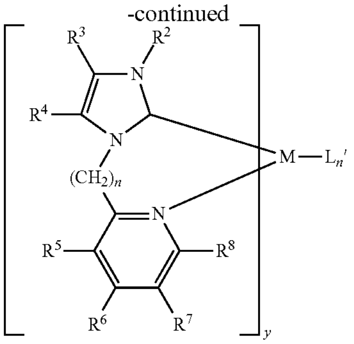

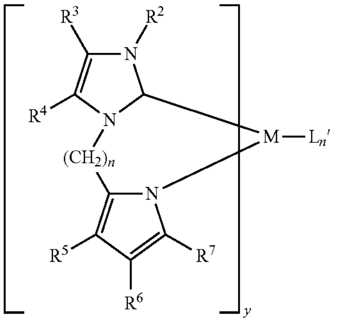

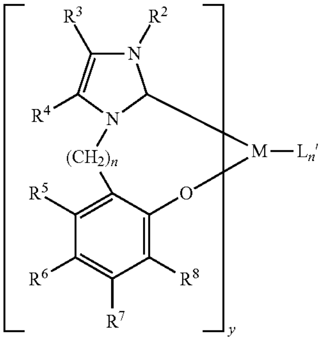

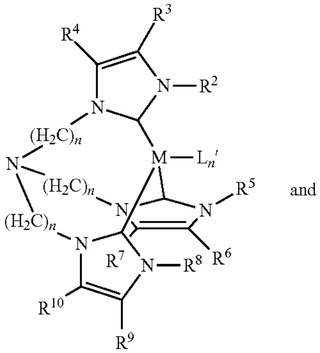

and

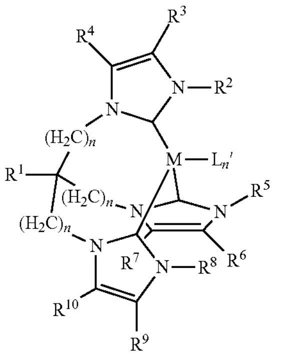

and saturated versions; y=1-4; n=0-5; $L_n$', and $R^1$-$R^{10}$ as defined above Particularly effective for the synthesis of metallocarbenes is the complexation of appropriate metal reagents by in-situ generated or isolated free carbenes such as imidazol-2-ylidenes (2) (see Scheme 1). These free carbene ligands may be conveniently generated from treatment of, for example, N,N'-disubstituted imidazolium salts with bases (e.g. potassium tert-butoxide, potassium hydride, etc.). Alkyl, aryl, and heteroatom-containing imidazoles, imidazolium salts, and carbenes are all known. The ancillary ligands bound to the metal center in the metallocarbene ($L_n$') may or may not be different from the ancillary ligands bound to the metal in the starting material ($L_n$). The ancillary ligand array on the metallocarbene ($L_n$') may also be further derivatized or modified in order to generate useful activators. Representative non-carbene groups as part of the ancillary ligand array can include halides, hydroxides, perhydroxides, alkoxides, acetates, ethers such as tetrahydrofuran, nitriles such as acetonitrile, trifluoromethanesulfonate, tetrafluoroborate, water, amines, phosphines, and bridging and terminal oxo ligands.

The following formation schemes are representative of methods to make the metallocarbene complexes of the present invention. The carbene ligand framework

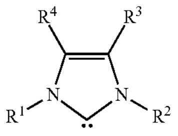

is used in the following schemes as an example only, any ligand framework such as those shown above can be employed.

Scheme 1

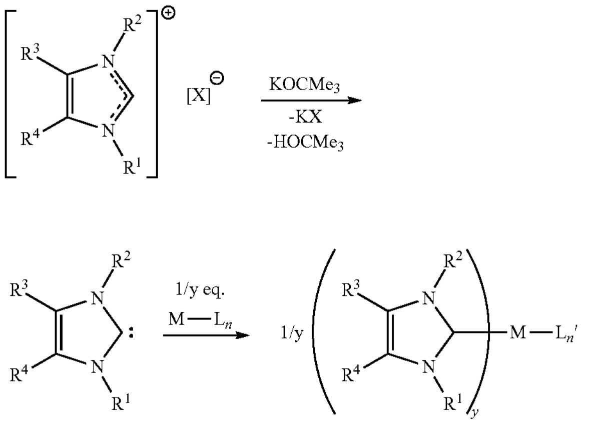

(2)

X = Cl, Br, I, $PF_6$

The ability to modify the carbene substituents (e.g. $R^1$-$R^4$ in Scheme 1) provides a means of controlling the activator solubility. The ability of the activator to bind or partition preferentially to a (typically organic) stain can improve the overall effectiveness of the activator for bleaching. Long-chain hydrocarbon groups on $R^1$-$R^4$ can make the activator more hydrophobic, useful for stain binding especially for stains such as those derived from agents with long chain hydrocarbons, such as sebum, lycopene, and beta-carotene. Inclusion of aromatic groups as part of $R^1$-$R^4$ can improve binding selectivity for stains with aromatic functionalities, such as coffee, tea, and many fruit and berry stains. Short-chain hydrocarbon groups or polyethylene glycol or polypropylene glycol functionalities on $R^1$-$R^4$ can make the catalyst more hydrophilic (and thus water soluble), useful fur anti-redeposition or dye transfer inhibition. Effective balancing of the hydrophobic and hydrophilic properties of the substituents can allow "tuning" of the activator solubility for different applications.

The ability to modify the carbene substituents (e.g. $R^1$-$R^4$ in Scheme 1) also provides a means of controlling the activator activity and selectivity. Reducing the steric bulk of the $R^1$ and/or $R^2$ substituents may allow greater substrate access to the metal center, thus potentially increasing the activity of an activator.

The ability to independently modify the solubility and reactivity of an activation or oxidation activator is especially useful.

Iron-carbene complexes in accordance with the present invention may be generated from treatment of iron-containing materials, such as iron-halides, with isolated or in-situ generated imidazol-2-ylidenes, Scheme 2; wherein $R^1$= —$(CH_2)_7CH_3$, —$(CH_2)_3CH_3$; $R^2$=—$CH_3$; $R^3$=$R^4$=H; Fe-$L_n$=$FeCl_2$; y=2].

Scheme 2

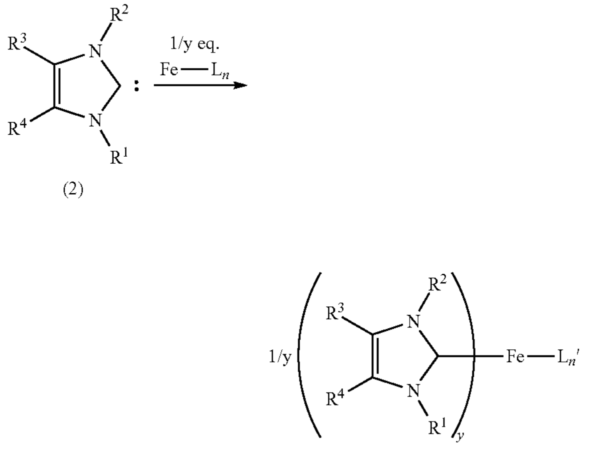

R groups other than the hydrogen, methyl-, butyl- and octyl-groups listed above are encompassed in the scope of this invention. Specifically, $R^1$-$R^4$ may comprise hydrogen or C1-C20 linear or branched hydrocarbons which may contain hetroatom substituents, including but not limited to methyl, chloromethyl, ethyl, isopropyl, tert-butyl, sec-butyl, n-butyl, pentyl, hexyl, cyclohexyl, heptyl, octyl, nonyl, lauryl, adamantyl, benzyl, phenyl, substituted phenyls such as chlorophenyl, dichlorophenyl, methylphenyl, nitrophenyl, aminophenyl, trimethylphenyl, diisopropylphenyl, methoxyphenyl, chlorophenyl, trifluoromethylphenyl, bis(trifluoromethyl)phenyl, pentafluorophenyl groups, and may furthermore have one or more heteroatom containing groups including but not limited to halides, amines, amides, pryidyls, ethers, aldehydes, ketones, phosphines, and sulfonates. $R^1$-$R^4$, as depicted in Scheme 2, may be the same or different. While the carbene ligands depicted in Schemes 1 and 2 are based on the unsaturated imidazol-2-ylidene, ligands based on the unsaturated 4,5-dimethylimidazol-2-ylidene, the saturated imidazolin-2-ylidene, as well as other cyclic or acyclic carbene ligands are encompassed by this invention. Also encompassed by this invention are carbene ligands based upon frameworks other than the specific examples provided in these schemes. Scheme 2 is exemplary and depicts a stoichiometric coordination of carbene ligands to the metal center appropriate for that specific scheme. This invention also encompasses metallocarbenes in which the product carbene: metal ratio differs from the carbene:metal ratio charged to the flask. Also encompassed by this invention are metallocarbenes requiring more than one synthetic step for synthesis from free carbene ligand to activator.

Although monometallic species are shown, this invention also encompasses polymetallic complexes, in which the metals and bound ligands may or may not be the same.

Iron-carbene complexes may also be generated by addition of $Fe(OTf)_2(solvent)_2$, (OTf=trifluoromethanesulfonate=$OSO_2CF_3$) to one or more equivalents of carbene ligand. In the resultant complexes, the triflate counter ions may either be covalently bound to the metal center, or be outer-sphere counter ions, with the remaining coordination site(s) on iron potentially bound by one or more solvent molecules (e.g. THF, $CH_3CN$, $H_2O$), as depicted in Scheme 3, wherein R=—$(CH_2)_7CH3$, —$(CH_2)_3$ $CH_3$, or some combination of inner-sphere and outer-sphere counterions or ligands.

Scheme 3

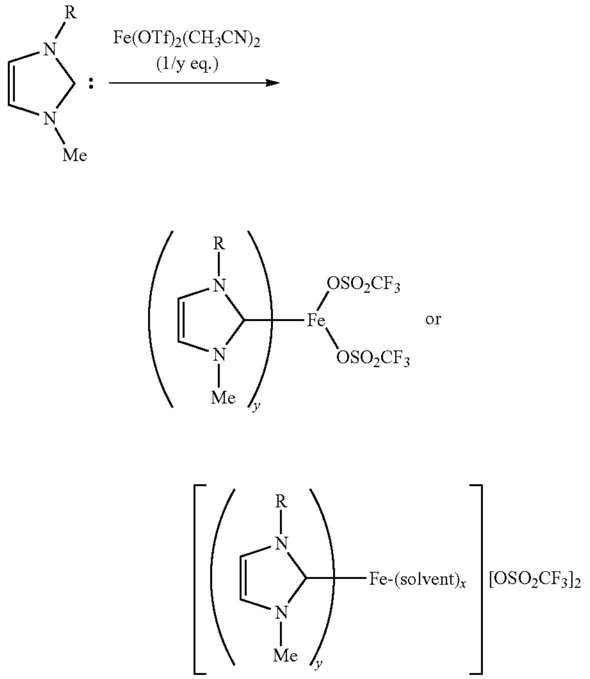

Other $L_n$ and $L_n'$ including but not limited to bromide, chloride, fluoride, iodide, ethoxide, cyclopentadienyl and substituted cyclopentadienyl, nitrate, carbonyl, oxalate, perchlorate, sulfate, acetate, tetrafluoroborate, triflate, and hexafluorophosphate are encompassed by this invention.

Manganese-carbene complexes may be generated by treatment of Mn-containing reagents, such as $MnCl_2$, with preformed or in-situ generated carbene ligand as shown in Scheme 4.

Scheme 4

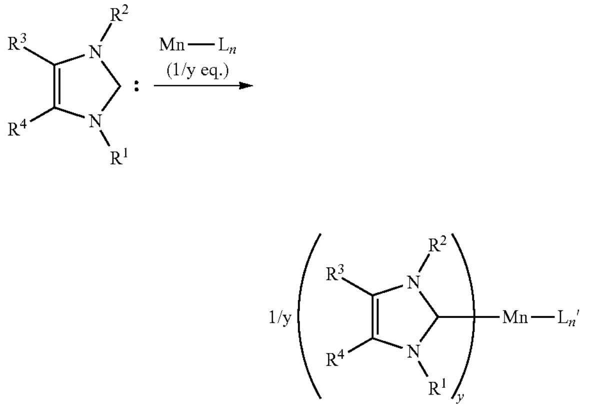

Alternate $L_n$ and $L_n'$ include but are not limited to chloride, bromide, fluoride, iodide, acetate, triflate, tetrafluoroborate, hexafluorophosphate, perchlorate, nitrate, sulfate, cyclopentadienyl and substituted cyclopentadienyl, and carbonyl.

The carbene ligands depicted in Schemes 3 and 4 are exemplary only and are based on the unsaturated imidazol-2-ylidene. Ligands based on the unsaturated 4,5-dimethylimidazol-2-ylidene, the saturated imidazolin-2-ylidene, as well as other cyclic or acyclic carbene ligands are encompassed by this invention. Also encompassed by this invention are carbene ligands based upon frameworks other than the specific examples provided herein.

Carbene:Mn stoichiometries including but not limited to 1:1, 2:1, 3:1, and 4:1 are also encompassed by this invention. Also encompassed are activators where $L_n'$ has been chemically modified from $L_n'$ upon metalation. $L_n'$ is $L_n$ or a modified $L_n$ wherein $L_n$ has been modified after metalation. Examples of modification of $L_n'$ include but are not limited to coordination of additional ligands (such as $H_2O$), removal of ligands, exchange of counterions, and replacement or incorporation of one or more ligands by oxidation or reduction.

Bis(manganese) and other poly(manganese) complexes containing carbene ligands are also encompassed by this invention. Particularly useful bis(manganese) frameworks include $(carbene)_y(L_n')Mn(\mu\text{-}O)_3Mn(L_n')(carbene)_y$, and $(carbene)_y(L_n')Mn(\mu\text{-}O)(\mu\text{-}O_2CCH_3)_2Mn(L_n')(carbene)_y$ in which the y and $L_n'$ may be the same or different and at least one y≥1. In bimetallic or polymetallic structures, two or more carbene ligands may be covalently bound through linkers other than the metal center(s).

The hydrogen peroxide activators of the present invention can include ligands containing two or more carbene functional groups, and can also include ligands with one or more carbene groups and one or more non-carbene groups capable of binding to the metal center. Bidentate carbene ligands include the pyridylalkyl-substituted imidazol-2-ylidene (structure 3), which can generate metallocarbene complexes according to the general procedure shown in Scheme 5.

Scheme 5

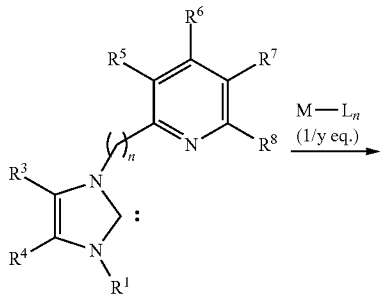

(3)

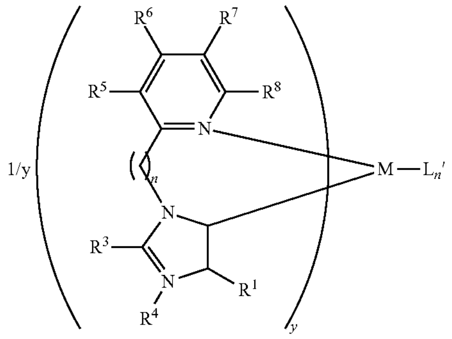

The procedure of scheme 5 is exemplary; ligands based on the unsaturated 4,5-dimethylimidazol-2-ylidene, the saturated imidazolin-2-ylidene, as well as other cyclic or acyclic carbene ligands are encompassed by this invention. $L_n$ and $L_n'$ encompassed by this invention include, but are not limited to, bromide, chloride, fluoride, iodide, ethoxide, nitrate, carbonyl, oxalate, perchlorate, sulfate, acetate, tetrafluoroborate, triflate, and hexafluorophosphate. Also encompassed by this invention are carbene ligands based upon frameworks other than the specific examples provided herein. The $R^1$-$R^8$ groups in structure 3 may furthermore contain one or more additional groups (such as amine, pyridine, or carbene groups) capable of binding to a metal center.

Other examples of metallocarbene complexes of the present invention include, but are not limited to, the species shown below, where M, $L_n'$, y, n, and $R^2$-$R^{11}$ are as defined above.

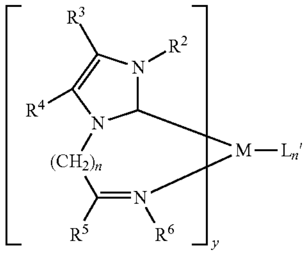

-continued

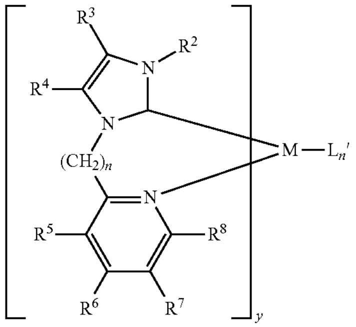

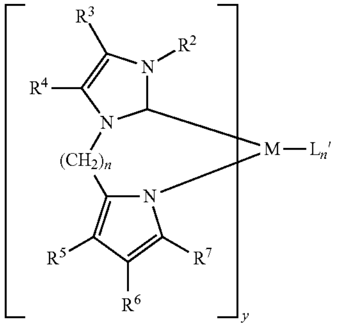

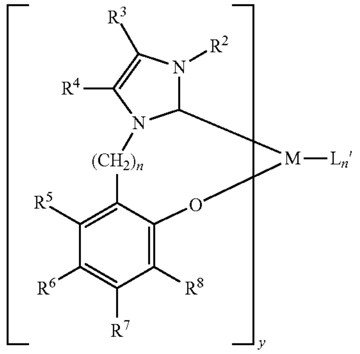

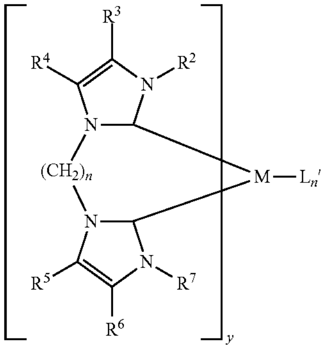

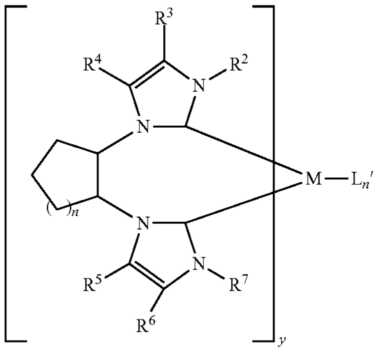

-continued

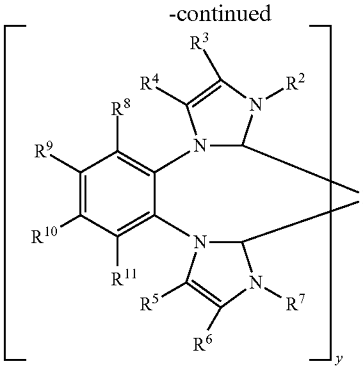

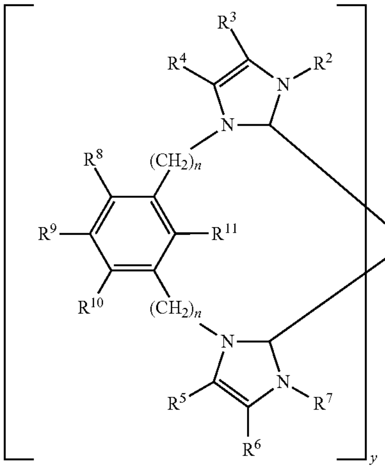

The carbene ligand substitutents of these bidentate carbene complexes are as defined herein above.

The hydrogen peroxide activators of the present invention can include tris(carbene) ligands and complexes. Examples of these complexes are structures 4 and 5. Structure 4 shows metal complex bound by three carbene groups, with the imidazol-2-ylidene fragments tethered to a central nitrogen atom. The covalent binding of multiple imidazol-2-ylidene fragments to a central atom should result in a structure where $R^2$, $R^5$, and $R^8$ reside on the side of the molecule accessible to hydrogen peroxide and to organic substrates. By changing the R substituents, the reactivity of the catalyst can be modified. The dashed line between the central N and the metal center is meant to denote the possibility of N electron lone pair donation to the metal, which will depend for each molecule on a combination of sterics and electronics (electron count and orbital availability).

Structure 5 also shows a metal complex bound by three carbene groups, with the imidazol-2-ylidene fragments tethered to a central carbon atom; the fourth substituent on the central carbon atom is the group denoted $R^1$. This metallocarbene catalyst framework possesses the beneficial attributes that the reactivity can be easily modified by changing the $R^2$, $R^5$, and $R^8$ groups, and that overall complex solubility can be independently modified by changing the other R substituents.

(4)

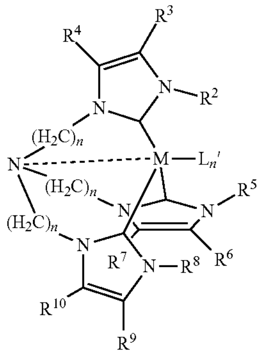

(5)

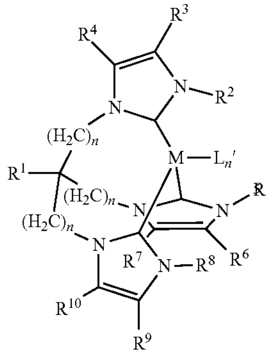

The carbene ligands depicted above are based on the unsaturated imidazol-2-ylidene. Ligands based on the unsaturated 4,5-dimethylimidazol-2-ylidene, the saturated imidazolin-2-ylidene, as well as other cyclic or acyclic carbene ligands are encompassed by this invention.

The general synthetic approach outlined in Scheme 6 has been used to generate N-centered carbene precursors which were used to generate tris(carbene) iron complexes from $FeCl_2$, $Fe(OTf)_2(CH_3CN)_2$, $Fe(OAc)_2$, and $Fe(BF_4)_2$.

Scheme 6

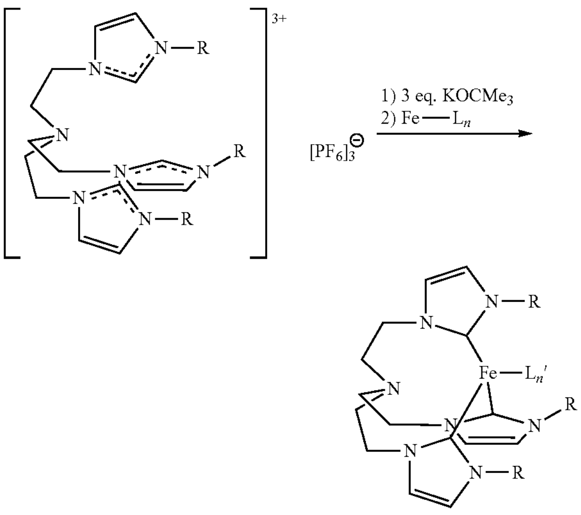

Complexes of polydentate carbene ligands such as the tris (carbene) (6) and the bis(carbene) (7) in accordance with the present invention include the following structures wherein M, $L_n'$, $R^2$ through $R^{10}$, and n are as defined herein above:

(6)

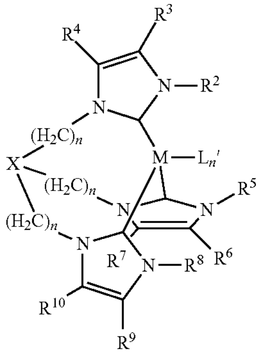

(7)

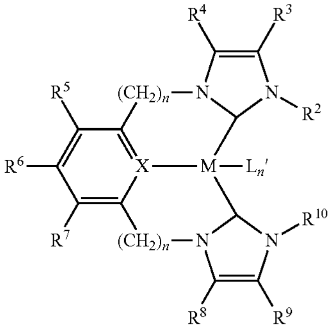

where for structure 6 X includes but is not limited to N, P, BR, and CR' (R'=H, alkyl, aryl, substituted alkyl, substituted aryl), and for structure 7 X includes but is not limited to N, P, and C.

The present invention encompasses the use of one metallocarbene activator and the use of mixtures of different metallocarbene activators. One or more metallocarbene activators may also be used in conjunction with one or more other non-carbene-type activators.

The compositions of the present invention are particularly useful for cleaning products, and especially useful for laundry detergents, auxiliary bleaches, dishwashing detergents, hard surface cleaners, and carpet cleaners.

As used herein detergent compositions include articles and cleaning and treatment compositions. As used herein, the term "cleaning and/or treatment composition" includes, unless otherwise indicated, tablet, granular or powder-form all purpose or "heavy-duty" washing agents, especially laundry detergents; liquid, gel or paste-form, or supported or adsorbed on woven or non-woven fibers, all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid, and rinse-aid types for household and institutional use. The compositions can also be in containers with multiple reservoirs or in unit dose packages, including those known in the art and those that are water soluble, water insoluble, and/or water permeable.

Suitable detergent ingredients include, but are not limited to, surfactants, builders, chelating agents, dye transfer inhibiting agents, dispersants, enzymes, enzyme stabilizers, bleach activators, hydrogen peroxide, sources of hydrogen peroxide, preformed peracids, polymeric dispensing agents, brighteners, suds suppressors, dyes, anti-corrosion agents, tarnish inhibitors, perfumes, fabric softeners, carriers, hydrotropes, processing aids, solvents, and/or pigments.

Examples of suitable bleaching agents include

1) Hydrogen peroxide, and sources of hydrogen peroxide, for example, inorganic perhydrate salts, including alkali metal salts such as sodium salts of perborate (usually mono- or tetrahydrate), percarbonate, persulfate, perphosphate, persilicate salts and mixtures thereof, atmospheric oxygen, organic peroxides, organic perhydroxides, and pre-formed peracids. In one aspect of the invention the hydrogen peroxide or inorganic perhydrate salts are selected from the group consisting of sodium salts of perborate, percarbonate and mixtures thereof, soaps; and
2) One or more bleach activators of the current invention. One or more additional bleach activators may include tetraacetylethylenediamine, nonanoyloxybenzene sulfonate, lauroyloxybenzene sulfonate, benzyloxybenzene sulfonate, quat imines, and quat nitriles.

This invention encompasses but is not limited to both formulations and use of metallocarbene complexes for peroxide activation, with effective concentrations of metallocarbene complexes ranging from 1 ppb to 99.99 weight %.

EXAMPLES

The following examples set out exemplary processes for making and the results of testing of metallocarbene complexes in accordance with the present invention. These examples are not intended to be limiting. The procedures and materials used could be easily obtained or duplicated by a person of ordinary skill in the art without undue experimentation.

Example 1

Manganese complexes of mono-carbene ligands in accordance with the present invention were generated by treatment of manganese(II) acetate with preformed or in-situ generated carbene ligands in accordance with the scheme:

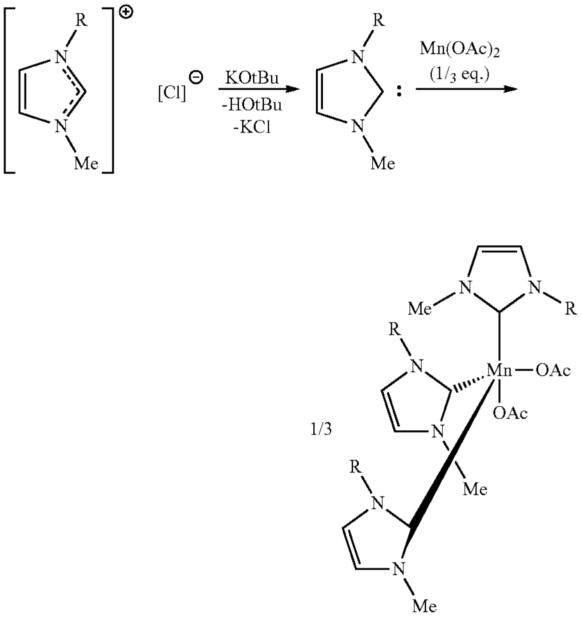

R = OCt, Bu

Example 2

Iron complexes of a pyridylmethyl-substituted carbene ligand were generated by treatment of $Fe(BF_4)_2$ with in-situ generated carbene ligands in accordance with the scheme:

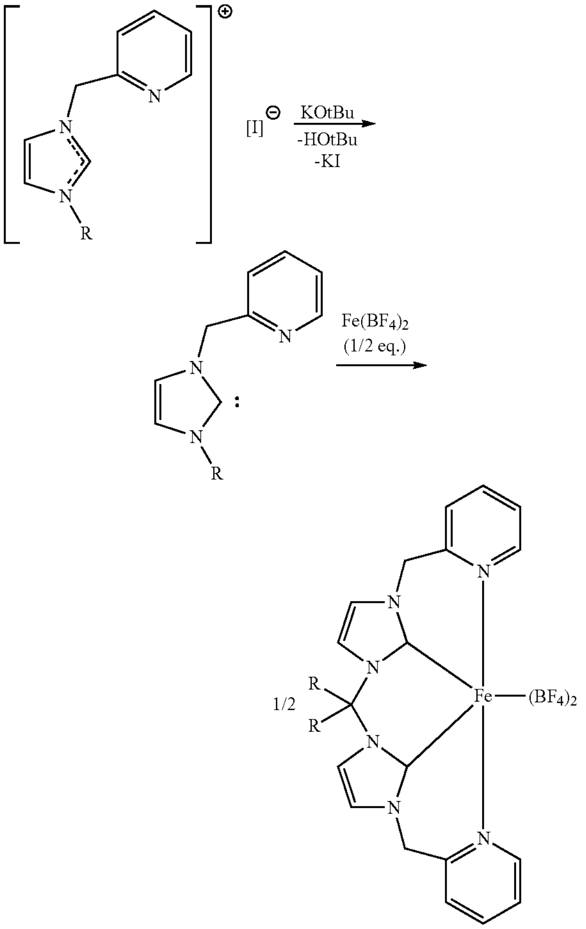

R = $CMe_3$

Example 3

Copper complexes of a tris(carbene) ligand in accordance with the present invention were generated by the treatment of CuCl with imidazol-2-ylidene in accordance with the scheme:

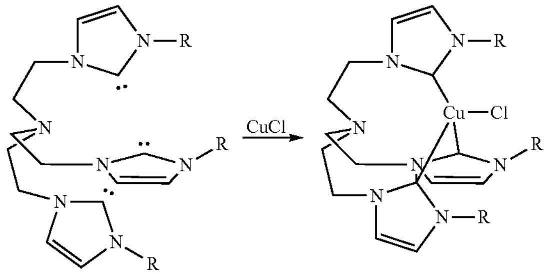

Example 4

Table 1 details the monodentate imidazol-2-ylidene-based activators which were synthesized of the general formula:

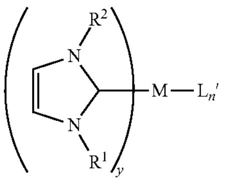

TABLE 1

| Activator | M | $R^1$ | $R^2$ | y | $L_n$ |
|---|---|---|---|---|---|
| 1 | Fe | n-Octyl | Methyl | 2 | $Cl_2$ |
| 2 | Fe | n-Octyl | Methyl | 2 | $(OTf)_2$ |
| 3 | Fe | n-Octyl | Methyl | 2 | $(OAc)_2$ |
| 4 | Fe | n-Octyl | Methyl | 2 | $(BF_4)_2$ |
| 5 | Mn | n-Octyl | Methyl | 3 | $Cl_2$ |
| 6 | Mn | n-Octyl | Methyl | 3 | $(OAc)_2$ |
| 7 | Cu | n-Octyl | Methyl | 1 | Cl |
| 8 | Fe | n-Butyl | Methyl | 2 | $Cl_2$ |
| 9 | Fe | n-Butyl | Methyl | 2 | $(OTf)_2$ |
| 10 | Fe | n-Butyl | Methyl | 2 | $(BF_4)_2$ |
| 11 | Mn | n-Butyl | Methyl | 3 | $Cl_2$ |
| 12 | Mn | n-Butyl | Methyl | 3 | $(OAc)_2$ |
| 13 | Mn | n-Butyl | Methyl | 3 | $(OTf)_2$ |
| 14 | Cu | n-Butyl | Methyl | 1 | Cl |

Activator 6 was prepared, in a manner representative of the preparation of the other Mn-based activators in Table 1 as follows: in a 200 ml round-bottom flask equipped with a magnetic stirrer was charged with 1-methyl-3-octylimidazolium chloride (4.252 g, 18.4 mmol), manganese(II) acetate, (1.063 g, 6.14 mmol), and 80 mL of tetrahydrofuran. Potassium tert-butoxide (2.067 g, 18.4 mmol) was slowly added to the mixture, and the solution stirred for 15 hours at room temperature. After filtration, solvent and organic volatiles were removed in vacuo, affording a viscous orange oil.

Activator 9 was prepared in a manner representative of the other Fe-based activators in Table 1 as follows: a 200 mL round-bottom flask equipped with a magnetic stirrer was charged with 1-butyl-3-methylimidazolium chloride (2.012 g, 11.5 mmol), ironbis(trifluoromethanesulfonate)bis(acetonitrile) (2.512 g, 5.76 mmol), and 80 mL of tetrahydrofuran. Potassium tert-butoxide (1.293 g, 11.5 mmol) was slowly added to the mixture, and the solution stirred for 15 hours at room temperature. After filtration, solvent and organic volatile were removed in vacuo. The product was obtained as a dark green paste.

Activator 14 was prepared in a manner representative of the other Cu-based activators in Table 1 as follows: a 100 mL round-bottom flask equipped with a magnetic stirrer was charged with 1-butyl-3-methylimidazolium chloride (0.300 g, 1.72 mmol), copper(I) chloride (0.169 g, 1.72 mmol), and 20 mL of tetrahydrofuran. Potassium tert-butoxide (0.218 g, 1.72 mmol) was slowly added to the mixture upon stirring, and the solution stirred for 15 hours at room temperature. After filtration, solvent and organic volatile were removed in vacuo, affording a very viscous yellow oil.

Example 5

Table 2 details the pyridylmethylimidazol-2-ylidene-based activators which were synthesized of the general formula:

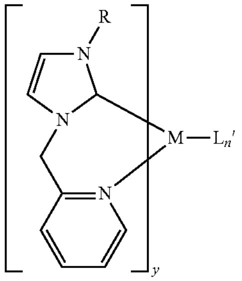

TABLE 2

| Activator | M | R | y | $L_n$ |
|---|---|---|---|---|
| 15 | Fe | t-Butyl | 2 | $Cl_2$ |
| 16 | Fe | t-Butyl | 2 | $(OTf)_2$ |
| 17 | Fe | t-Butyl | 2 | $(BF_4)_2$ |
| 18 | Mn | t-Butyl | 2 | $Cl_2$ |
| 19 | Mn | t-Butyl | 2 | $(OAc)_2$ |
| 20 | Cu | t-Butyl | 1 | Cl |

Activator 15 was prepared, in a manner representative of the preparation of the other activators in Table 2 as follows: in a 50 mL round-bottom flask equipped with a magnetic stirrer was charged with 1-tert-butyl-3-midylmethylimidazolium iodide (300 mg, 0.874 mmol), iron (II) chloride (55 mg, 0.437 mmol), and 20 mL of tetrahydrofuran. Potassium tert-butoxide (98.1 mg, 0.874 mmol) was added to the flask and the solution stirred for 15 hours at room temperature. Solvent and volatiles were removed from the reaction mixture under reduced pressure, and the non-volatiles were dissolved in dichloromethane (~30 mL). Solids were removed by filtration of the dichloromethane solution, and solvent was then removed to yield iron bis(1-t-butyl-3-pyridylmethylimidazol-2-ylidene)dichloride as an orange powder. The crude material was then recrystallized from dichloromethane and hexane (~10 mL).

Example 6

Table 3 details the tris[(imidazol-2-ylidene)alkyl]amine-based activators which were synthesized of the general formula:

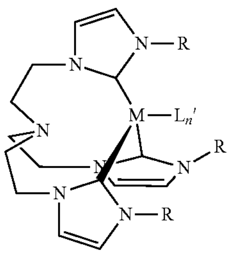

TABLE 3

| Activator | M | R | $L_n$ |
|---|---|---|---|
| 21 | Fe | t-Butyl | $Cl_2$ |
| 22 | Fe | t-Butyl | $(OTf)_2$ |
| 23 | Fe | t-Butyl | $(BF_4)_2$ |
| 24 | Mn | t-Butyl | $Cl_2$ |

TABLE 3-continued

| Activator | M | R | $L_n$ |
|---|---|---|---|
| 25 | Mn | t-Butyl | $(OAc)_2$ |
| 26 | Cu | t-Butyl | Cl |

Activator 25 was prepared, in a manner representative of the preparation of the other activators in Table 3 as follows: a solution of potassium tert-butoxide (0.32 g, 5.63 mmol) in tetrahydrofuran (15 mL) was added dropwise to a suspension of tris((tert-butylimidazolium)ethyl)amine tris(hexafluorophosphate) (1.700 g, 1.88 mmol) in tetrahydrofuran (20 mL) in a 200 mL round-bottom flask equipped with a magnetic stirrer. After stirring for 1 hour, the solution was evaporated to dryness under vacuum. To the solid residue was added 40 mL of diethyl ether, and the suspension stirred for about 5 minutes. After filtration, volatiles were removed under vacuum. The solid residue was then dissolved in about 50 mL of tetrahydrofuran, to which solid manganese(II) acetate (0.325 g, 1.88 mmol) was added. The mixture was then stirred for 15 hours at room temperature, filtered, and the filtrate dried in vacuo to yield a yellow solid.

Comparable processes were used to prepare the other M-carbene complexes in these examples.

Representative activators, in accordance with the present invention, described above were evaluated for water solubility and for cleaning performance.

Example 7

Water-solubility was assessed by charging a small amount (~15 mg) of material to a glass vial and adding ~2 mL of water. Materials that appeared largely insoluble are denoted with a (1), and materials with higher solubility are denoted with a (2).

TABLE 4

| Activator | Solubility |
|---|---|
| 1 | 1 |
| 2 | 2 |
| 8 | 1 |
| 9 | 2 |
| 21 | 1 |
| 22 | 2 |
| 25 | 2 |

Example 8

Cleaning performance was evaluated via differences in CIE lightness (L) and color parameter (a, b) reflectance between stained spots on an EMPA 102 stain sheet [Test Fabrics, Pittiston, Pa.] and an unwashed blank cotton spot (reference), recorded on a Datacolor Spectraflash SF650X spectrometer. $\Delta E^*_{unwashed,reference}$ was then calculated using Eq. 1.

$$\Delta E^*_{unwashed,reference} = \sqrt{(L_{unwashed} - L_{reference})^2 + (a_{unwashed} - a_{reference})^2 + (b_{unwashed} - b_{reference})^2} \quad \text{(Eq. 1)}$$

The test procedure comprised adding 1 L of tap water to a 2-L stainless steel beaker, and placing the beaker in a temperature-regulated water bath (Terg-o-Tometer [Instrument Marketing Services, Inc., Fairfield, N.J.]) with vertical impeller agitation. The beaker water pH was adjusted with aqueous NaOH solution. Aqueous hydrogen peroxide was added to the beaker to a concentration of 0.0016 M, and agitated for one minute. Activator was charged to a glass vial along with 2 mL of tap water, the vial contents added to the beaker, and the beaker contents agitated for one minute. One EMPA stain sheet was added to the beaker, and the beaker contents agitated for 30 minutes. The beaker contents, except for the stain sheet, were then discarded, and the stain sheet rinsed twice (5 minutes each) with fresh tap water (1 L) in the beaker. The sheet was then air-dried for 40 minutes.

Following drying, the differences in L, a, and b between an unwashed blank cotton spot (reference) and the washed stained spots were recorded, and $\Delta E^*_{washed,reference}$ calculated according to Eq. 2.

$$\Delta E^*_{washed,reference} = \sqrt{(L_{washed} - L_{reference})^2 + (a_{washed} - a_{reference})^2 + (b_{washed} - b_{reference})^2} \quad \text{(Eq. 2)}$$

The quantity $\Delta\Delta E^*$, defined as $\Delta E^*_{unwashed,reference} - \Delta E^*_{washed,reference}$ (Eq. 3), was calculated; higher values of $\Delta\Delta E^*$ correspond to better cleaning performance. All Terg-o-Tometer experiments were conducted in triplicate, with the average for the 3 runs ($\Delta\Delta E^*_{avg}$; Eq. 4) used to evaluate cleaning performance.

$$\Delta\Delta E^*_{avg} = \frac{\Delta\Delta E^*_{run1} + \Delta\Delta E^*_{run2} + \Delta\Delta E^*_{run3}}{3} \quad \text{(Eq. 4)}$$

Table 5 summarizes $[(\Delta\Delta E^*_{avg,activator}) - (\Delta\Delta E^*_{avg,H2O2})]$, the difference in average cleaning performance between the combination water plus hydrogen peroxide plus activator ($\Delta\Delta E^*_{avg,activator}$) versus the combination water plus hydrogen peroxide ($\Delta\Delta E^*_{avg,H2O2}$) of selected activators on typically bleachable stains.

TABLE 5

| Activator | pH | Temp ° C. | Activator concentration, mol/L | Curry | Red Wine | Blood | Dessert | Tea | Beta-Carotene | Grass |
|---|---|---|---|---|---|---|---|---|---|---|
| 2 | 7 | 25 | 0.000016 | −1 | 3 | 9 | 5 | 1 | 0 | 1 |
| 6 | 7 | 25 | 0.000016 | 1 | 3 | 14 | 9 | 0 | 1 | 3 |
| 2 | 7 | 25 | 0.00016 | −1 | −3 | 7 | 10 | −2 | −5 | 4 |
| 9 | 10 | 25 | 0.000016 | −3 | 5 | −5 | 9 | 4 | 2 | 2 |
| 9 | 10 | 25 | 0.00016 | −3 | 2 | −3 | 9 | 4 | −4 | 2 |
| 4 | 10 | 25 | 0.000016 | 5 | 1 | 6 | 17 | 0 | 5 | 2 |
| 17 | 10 | 25 | 0.000016 | 6 | 3 | 8 | 19 | 2 | 5 | 2 |
| 25 | 10 | 25 | 0.000016 | 8 | 1 | 7 | 20 | 1 | −1 | 2 |
| 2 | 7 | 49 | 0.000016 | −7 | 2 | −6 | 2 | 0 | 4 | 1 |
| 12 | 10 | 49 | 0.000016 | −1 | 4 | 4 | 5 | 2 | −4 | 3 |
| 17 | 10 | 49 | 0.000016 | 4 | 1 | 7 | 15 | −1 | 1 | 3 |
| 25 | 10 | 49 | 0.000016 | 11 | −1 | 8 | 13 | −1 | −5 | 4 |
| 25 | 10 | 49 | 0.00016 | 12 | −7 | 3 | 12 | −9 | −10 | 2 |

Table 6 summarizes $[(\Delta\Delta E^*_{avg,activator}) - (\Delta\Delta E^*_{avg,H2O2})]$, the difference in average cleaning performance between the combination water plus hydrogen peroxide plus activator ($\Delta\Delta E^*_{avg,activator}$) versus the combination water plus hydrogen peroxide ($\Delta\Delta E^*_{avg,H2O2}$) of selected activators on typically non-bleachable stains.

TABLE 6

| Activator | pH | Temp ° C. | Activator concentration, mol/L | Make-Up | Spaghetti Sauce | Peat | Animal Fat & Dye | Baby Food | Clay | Butter | Engine Oil |
|---|---|---|---|---|---|---|---|---|---|---|---|
| 6 | 7 | 25 | 0.00016 | 14 | 1 | −2 | 7 | 1 | 6 | −5 | 2 |
| 2 | 9.5 | 25 | 0.000016 | −5 | 10 | −2 | 6 | −1 | −3 | 6 | 3 |
| 6 | 10 | 25 | 0.000016 | 13 | −1 | 1 | 4 | 1 | 0 | −1 | 0 |
| 19 | 10 | 25 | 0.000016 | 8 | −2 | 2 | 6 | 2 | 4 | 1 | 1 |
| 12 | 10 | 25 | 0.000016 | 12 | −8 | 1 | 1 | −1 | 1 | 0 | 11 |
| 4 | 10 | 25 | 0.000016 | 7 | −3 | 6 | 5 | 2 | 5 | 4 | 8 |
| 17 | 10 | 25 | 0.000016 | 2 | −7 | 7 | 19 | 0 | 3 | 2 | 9 |
| 25 | 10 | 25 | 0.000016 | 7 | 1 | 6 | 12 | 2 | 4 | 0 | 12 |
| 6 | 7 | 49 | 0.000016 | 12 | 10 | 0 | 13 | 2 | −1 | −3 | −2 |
| 2 | 7 | 49 | 0.00016 | 2 | 5 | −3 | 19 | 3 | −2 | −7 | 4 |
| 4 | 10 | 49 | 0.000016 | 3 | −2 | 7 | 6 | −2 | 6 | 4 | 3 |
| 17 | 10 | 49 | 0.000016 | −4 | −2 | 6 | 12 | −3 | 4 | 5 | 6 |

Tables 7 summarizes [$(\Delta\Delta E^*_{avg,activator})-(\Delta\Delta E^*_{avg,Mn(TACN)})$], the difference in average cleaning performance between water plus hydrogen peroxide plus activator [$(\Delta\Delta E^*_{avg,activator})$ versus the combination water plus hydrogen peroxide plus 0.000012 M $Mn_2(TACN)_2(O)_3(PF_6)_2$, $(\Delta\Delta E^*_{avg,Mn(TACN)})$ (synthesized according to *J. Chem. Soc. Dalton Trans.*, 1996, 353; TACN=1,3,5-trimethyl-1,3,5-triazacyclononane).

TABLE 7

| Activator | pH | Temp ° C. | Activator concentration, mol/L | Make-Up | Curry | Red Wine | Spaghetti Sauce | Blood | Dessert | Tea | Beta-Carotene | Animal Fat & Dye |
|---|---|---|---|---|---|---|---|---|---|---|---|---|
| 6 | 7 | 25 | 0.000016 | 8 | 11 | 4 | 2 | 4 | 5 | 2 | −7 | 6 |
| 2 | 9.5 | 25 | 0.000016 | −5 | −20 | 2 | 8 | −14 | 9 | −1 | 0 | 6 |
| 2 | 7 | 49 | 0.00016 | −8 | −10 | −3 | 0 | −1 | −16 | −3 | 9 | 6 |
| 17 | 10 | 49 | 0.00016 | −6 | −18 | −3 | −9 | 8 | 6 | −7 | −5 | 3 |
| 25 | 10 | 49 | 0.000016 | −2 | 11 | −1 | −1 | 8 | 13 | −1 | −5 | 12 |

Table 8 summarizes [$(\Delta\Delta E^*_{avg,activator})-(\Delta\Delta E^*_{avg,H2O2})$], the difference in average cleaning performance between the combination water plus hydrogen peroxide plus activator $(\Delta\Delta E^*_{avg,activator})$ versus the combination water plus hydrogen peroxide $(\Delta\Delta E^*_{avg,H2O2})$.

TABLE 8

| Activator | pH | Temp ° C. | Activator concentration, mol/L | Make-Up | Curry | Red Wine | Spaghetti Sauce | Blood | Dessert | Peat | Tea | Beta-Carotene | Grass | Animal Fat & Dye | Baby Food | Clay | Butter | Oil |
|---|---|---|---|---|---|---|---|---|---|---|---|---|---|---|---|---|---|---|
| 6 | 7 | 25 | 0.000016 | 13 | 1 | 3 | −2 | 14 | 9 | −2 | 0 | 1 | 3 | 7 | 1 | 0 | 1 | 1 |
| 25 | 10 | 25 | 0.000016 | 7 | 8 | 1 | 1 | 7 | 20 | 6 | 1 | −1 | 2 | 12 | 2 | 4 | 0 | 12 |
| 17 | 10 | 25 | 0.000016 | 2 | 6 | 3 | −7 | 8 | 19 | 7 | 2 | 5 | 2 | 9 | 0 | 3 | 2 | 9 |
| 10 | 10 | 25 | 0.000016 | 6 | 4 | 2 | −5 | 7 | 15 | 2 | 0 | 5 | 1 | 5 | 2 | 4 | 1 | 5 |
| 2 | 7 | 49 | 0.000016 | 10 | −7 | 2 | 8 | −6 | 2 | 2 | 0 | 4 | 1 | 2 | 1 | −3 | 0 | 4 |
| 4 | 10 | 49 | 0.000016 | 3 | 6 | −1 | −2 | 7 | 13 | 7 | −5 | 3 | 2 | 6 | −2 | 6 | 4 | 3 |
| 10 | 10 | 49 | 0.000016 | 4 | 5 | 0 | −7 | 8 | 13 | 3 | −2 | −1 | 2 | 7 | −5 | 1 | 0 | 3 |
| 2 | 9.5 | 25 | 0.00016 | −10 | −2 | −3 | 1 | −5 | −6 | −5 | −1 | −8 | −2 | −11 | −5 | −9 | 2 | 2 |
| 6 | 7 | 49 | 0.00016 | 5 | −7 | −5 | 6 | −10 | −9 | −6 | −5 | −6 | −3 | −3 | −3 | −10 | −16 | −2 |
| 6 | 9.5 | 25 | 0.00016 | −12 | 5 | −6 | −1 | −2 | −5 | −8 | −4 | −10 | −3 | 0 | −5 | −8 | −1 | −6 |
| 2 | 10 | 49 | 0.00016 | −9 | −1 | −4 | −1 | 0 | −1 | −1 | −2 | −8 | 1 | −3 | −8 | 0 | −4 | 3 |
| 2 | 10 | 25 | 0.00016 | 1 | −10 | −2 | −12 | −5 | 0 | −3 | −1 | −5 | −1 | −2 | −5 | −3 | −2 | 4 |

While the present invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What is claimed is:

1. A bleaching composition comprising a peroxy compound and one or more activator present in an effective amount to activate the peroxy compound, present in an effective amount to accomplish bleaching or cleaning or oxidation, the activator comprising one or more metallocarbenes of the general structure:

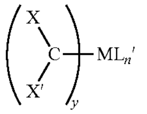

where M represents a metal selected from the group consisting of Fe, Mn, Cu, Co, Mo, V and Ti, C represents the carbene carbon bound to the metal center, X is nitrogen, X' is carbon, wherein both X and X' may be substituted with hydrogen and or C1-C20 linear or branched hydrocarbons which may contain heteroatom substituents and which may form or be part of a cyclic structure, $L_n$, ' represents one or more ligands which may or may not include one or more metal centers, and where y>1.

2. The bleaching composition of claim 1 wherein said ligand, $L_n$' is selected from the group $H_2O$, ROH, ROR, $NR_3$, $PR_3$, RCN, $HO^-$, $HS^-$, $HOO^-$, $RO^-$, $RCOO^-$, $F_3CSO_3^-$, $BF_4^-$, $BP_4^-$, $PF_6^-$, $ClO_4^-$, $OCN^-$, $SCN^-$, $NR_2^-N_3^-$, $CN^-$, $F^-$, $Cl^-$, $Br^-$, $I^-$, $H^-$, $R^-$, $O_2^-$, $O^{2-}$, $NO_2^-$, $SO_4^{2-}$, $RSO_3^-$, $SO_3^{2-}$, $RBO_2^{2-}PO_4^{3-}$, organic phosphates, organic phosphonates, organic sulfates, organic sulfonates, pyridines, bipyridines, terpridines, pyrazines, pyrazoles, imidazoles, benzimidazoles, pyrimidines, triazoles, thiazoles and mixtures thereof, wherein R can be the same or different and selected from the group consisting of hydrogen, alkyl, aryl, substituted alkyl, substituted aryl, and mixtures thereof.

3. The bleaching composition of claim 1 wherein XX'C is the group

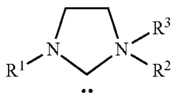

wherein $R^1$, $R^2$ and $R^3$ are the same or different and selected from the group consisting of hydrogen, alkyl, aryl, substituted alkyl, substituted aryl, heteroatom, substituted heteroatom and mixtures thereof.

4. The bleaching composition of claim 1 wherein y is from 1 to 4.

5. The bleaching composition of claim 1 wherein said peroxy compound is selected form the group consisting of hydrogen peroxide, alkylhydroperoxides, dialkylperoxides, peracids, dioxygen, sodium percarbonate, sodium perborate, and mixtures thereof.

6. A method of activating a peroxy bleach compound comprising adding to said peroxy compound one or more metallocarbenes of the general structure:

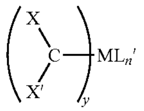

where M represents a metal selected from the group consisting of Fe, Mn, Cu, Co, Mo, V and Ti, C represents the carbene carbon bound to the metal center, X is nitrogen, X' is carbon, wherein both X and X' may be substituted with hydrogen and or C1-C20 linear or branched hydrocarbons which may contain heteroatom substituents and which may form or be part of a cyclic structure and may furthermore be part of a cyclic structure, $L_n$' represents one or more ligands which may or may not include one or more metal centers, and where y≥1.

7. The method of claim 6 wherein said ligand, $L_n$' is selected from the group $H_2O$, ROH, ROR, $NR_3$, $PR_3$, RCN, $HO^-$, $HS^-$, $HOO^-$, $RO^-$, $RCOO^-$, $F_3CSO_3^-$, $BF_4^-$, $BPh_4^-$, $PF_6^-$, $ClO_4^-$, $OCN^-$, $SCN^-$, $NR_2^-$, $N_3^-$, $CN^-$, $F^-$, $Cl^-$, $Br^-$, $I^-$, $H^-$, $R^-$, $O_2^-$, $O^2$ $^-$, $NO_3^-$, $NO_2$ $^-$, $SO_4^{2-}$, $RSO_3^-$, $SO_3^{2-}$, $RBO_2^{2-}$, $PO_4^{3-}$organic phosphates, organic phosphonates, organic sulfates, organic sulfonates, pyridines, bipyTidines, terpyridines, pyrazines, pyrazoles, imidazoles, benzimidazoles, pyrimidines, triazoles, thiazoles and mixtures thereof; wherein R can be the same or different and selected from the group consisting of hydrogen, alkyl, aryl, substituted alkyl, substituted aryl, and mixtures thereof.

8. The method of claim 6 wherein XX'C is the group

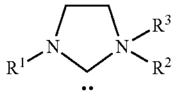

wherein $R^1$, $R^2$ and $R^3$ are the same or different and selected from the group consisting of hydrogen, alkyl, aryl, substituted alkyl, substituted aryl, heteroatom, substituted heteroatom and mixtures thereof.

9. The method of claim 6, wherein y is from 1 to 4.

10. The method of claim 6 wherein said peroxy compound is selected from the group consisting of hydrogen peroxide, alkylhydroperoxides, dialkylperoxides, peracids, dioxygen, sodium percarbonate, sodium perborate, and mixtures thereof.

* * * * *